United States Patent
Sawada et al.

(10) Patent No.: US 11,352,408 B2
(45) Date of Patent: Jun. 7, 2022

(54) ANTITUMOR PEPTIDE HAVING PD-1 SIGNAL SEQUENCE AND UTILIZATION THEREOF

(71) Applicants: TOAGOSEI CO., LTD., Tokyo (JP); NATIONAL UNIVERSITY CORPORATION NAGOYA UNIVERSITY, Aichi (JP)

(72) Inventors: Makoto Sawada, Aichi (JP); Nahoko Baileykobayashi, Ibaraki (JP); Tetsuhiko Yoshida, Ibaraki (JP)

(73) Assignees: Toagosei Co., Ltd., Tokyo (JP); National University Corporation Nagoya University, Aichi (JP)

( * ) Notice: Subject to any disclaimer, the term of this patent is extended or adjusted under 35 U.S.C. 154(b) by 242 days.

(21) Appl. No.: 16/499,477

(22) PCT Filed: Mar. 27, 2018

(86) PCT No.: PCT/JP2018/012565
§ 371 (c)(1),
(2) Date: Sep. 30, 2019

(87) PCT Pub. No.: WO2018/181390
PCT Pub. Date: Oct. 4, 2018

(65) Prior Publication Data
US 2020/0055915 A1     Feb. 20, 2020

(30) Foreign Application Priority Data
Mar. 31, 2017 (JP) .............................. JP2017-070758

(51) Int. Cl.
| A61P 35/00 | (2006.01) |
| C07K 19/00 | (2006.01) |
| A61K 38/00 | (2006.01) |
| C07K 14/705 | (2006.01) |

(52) U.S. Cl.
CPC ............ *C07K 14/705* (2013.01); *A61P 35/00* (2018.01); *C07K 19/00* (2013.01); *A61K 38/00* (2013.01); *C07K 2319/02* (2013.01); *C07K 2319/10* (2013.01)

(58) Field of Classification Search
CPC .............................. C07K 14/405; C07K 19/00
See application file for complete search history.

(56) References Cited

U.S. PATENT DOCUMENTS

2013/0079273 A1    3/2013    Yoshida et al.

FOREIGN PATENT DOCUMENTS

| EP | 1537878 | 6/2005 |
| WO | 2004004771 A1 | 1/2004 |
| WO | 2011152524 A1 | 12/2011 |
| WO | 2017162797 A1 | 9/2017 |

OTHER PUBLICATIONS

Kobayashi et al., "PO-409: Signal peptide of PD-1 inhibits cancer cell growth", Poster Presentation, vol. 3, Jun. 29, 2018, pp. A183-A183, XP55748421.
Extended European Search Report, dated Nov. 19, 2020, 8 pages.
International Search Report (English) and Written Opinion dated Jun. 19, 2018, from International Application No. PCT/JP2018/012565, 9 pages.
Hopkins et al. Nat Rev Cancer, 2016, vol. 12(4), p. 1-31.
Chen et al. Immunity, 2013, vol. 39, p. 1-10.
Ikebuchi et al. Microbiol Immunol, 2010, vol. 54, p. 291-298.

*Primary Examiner* — Elly-Gerald Stoica
(74) *Attorney, Agent, or Firm* — Meunier Carlin & Curfman LLC

(57) ABSTRACT

Provide is an artificially synthesized antitumor peptide that may suppress proliferation of tumor cells. The peptide provided is a synthetic peptide that contains both (1) an amino acid sequence that forms a signal peptide of a membrane protein, programmed cell death-1 (PD-1), or a modified amino acid sequence thereof in which 1, 2 or 3 amino acid residues deleted from, substituted in or added to the above amino acid sequence; and (2) an amino acid sequence that serves as a cell penetrating peptide (CPP), and wherein the synthetic peptide comprises a total of 100 or fewer amino acid residues.

3 Claims, No Drawings
Specification includes a Sequence Listing.

```
                         SEQUENCE LISTING

<160> NUMBER OF SEQ ID NOS: 30

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Met Gln Ile Pro Gln Ala Pro Trp Pro Val Val Trp Ala Val Leu Gln
1               5                   10                  15

Leu Gly Trp Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Met Trp Val Arg Gln Val Pro Trp Ser Phe Thr Trp Ala Val Leu Gln
1               5                   10                  15

Leu Ser Trp Gln
            20

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide

<400> SEQUENCE: 3

Met Gly Thr Pro Arg Ala Leu Trp Pro Leu Val Trp Ala Val Leu Gln
1               5                   10                  15

Leu Gly Cys Trp Pro Gly Trp Leu Leu Glu Ala Ser Ser
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic peptide

<400> SEQUENCE: 4

Met Gly Thr Pro Arg Ala Leu Trp Pro Leu Val Trp Ala Val Leu Gln
1               5                   10                  15

Leu Gly Cys Trp Pro Gly Trp Leu Leu Glu Ala Ser Ser
            20                  25

<210> SEQ ID NO 5
<211> LENGTH: 24
<212> TYPE: PRT
<213> ORGANISM: Artificial Sequence
<220> FEATURE:
<223> OTHER INFORMATION: Synthetic peptide
```

```
<400> SEQUENCE: 5

Met Gly Thr Pro Arg Ala Pro Trp Pro Leu Val Trp Ala Val Leu Gln
1               5                   10                  15

Leu Gly Trp Trp Pro Gly Trp Leu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Met Gln Ile Pro Gln Ala Pro Trp Pro Val Val Trp Ala Val Leu Gln
1               5                   10                  15

Leu Gly Trp Arg
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Met Val Val Gln Gln Val Pro Trp Ser Phe Thr Trp Ala Val Leu Gln
1               5                   10                  15

Leu Ser Trp Gln
            20

<210> SEQ ID NO 8
<211> LENGTH: 14
<212> TYPE: PRT
<213> ORGANISM: Artificial sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 19
<212> TYPE: PRT
<213> ORGANISM: Artificial sequence
<220> FEATURE:
<223> OTHER INFORMATION: Synthetic peptide

<400> SEQUENCE: 9

Met Ala Lys Ser Ile Arg Ser Lys His Arg Arg Gln Met Arg Met Met
1               5                   10                  15

Lys Arg Glu

<210> SEQ ID NO 10
<211> LENGTH: 16
<212> TYPE: PRT
<213> ORGANISM: Artificial sequence
<220> FEATURE:
<223> OTHER INFORMATION: Synthetic peptide

<400> SEQUENCE: 10

Met Ala Arg Arg Arg Arg His Arg Gly Pro Arg Arg Pro Arg Pro Pro
```

```
1               5              10              15
```

<210> SEQ ID NO 11
<211> LENGTH: 19
<212> TYPE: PRT
<213> ORGANISM: Artificial sequence
<220> FEATURE:
<223> OTHER INFORMATION: Synthetic peptide

<400> SEQUENCE: 11

Gly Arg Cys Arg Arg Leu Ala Asn Phe Gly Pro Arg Lys Arg Arg
1               5                   10                  15

Arg Arg Arg

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

Arg Arg Arg Lys Arg Asn Arg Asp Ala Arg Arg Arg Arg Lys Gln
1               5                   10                  15

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Met Gln Arg Lys Pro Thr Ile Arg Arg Lys Asn Leu Arg Leu Arg Arg
1               5                   10                  15

Lys

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Ile Met Arg Arg Arg Gly Leu
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Lys Lys Leu Lys Lys Arg Asn Lys
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 16

Arg Arg Arg Ala Asn Asn Arg Arg Arg
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

Arg Lys Lys Arg Lys Lys Lys
1               5

<210> SEQ ID NO 18
<211> LENGTH: 15
<212> TYPE: PRT
<213> ORGANISM: Artificial sequence
<220> FEATURE:
<223> OTHER INFORMATION: Synthetic peptide

<400> SEQUENCE: 18

Lys Arg Lys Gly Lys Leu Lys Asn Lys Gly Ser Lys Arg Lys Lys
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

Ser Lys Arg Leu Ser Ser Arg Ala Arg Lys Arg Ala Ala Lys Arg Arg
1               5                   10                  15

Leu Gly

<210> SEQ ID NO 20
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

Lys Arg Pro Arg Arg Arg Pro Ser Arg Pro Phe Arg Lys Pro
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Lys Lys Arg Thr Leu Arg Lys Asn Asp Arg Lys Lys Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
```

<400> SEQUENCE: 22

Trp Arg Arg Gln Ala Arg Phe Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Arg Lys Lys Arg Arg Gln Arg Arg Arg
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Tyr Ala Arg Ala Ala Ala Arg Gln Ala Arg Ala
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Lys Gly Arg Gln Val Lys Val Trp Phe Gln Asn Arg Met Lys Trp
1               5                   10                  15

Lys Lys

<210> SEQ ID NO 26
<211> LENGTH: 33
<212> TYPE: PRT
<213> ORGANISM: Artificial Sequence
<220> FEATURE:
<223> OTHER INFORMATION: Synthetic peptide

<400> SEQUENCE: 26

Met Gln Ile Pro Gln Ala Pro Trp Pro Val Val Trp Ala Val Leu Gln
1               5                   10                  15

Leu Gly Trp Arg Lys Lys Arg Thr Leu Arg Lys Asn Asp Arg Lys Lys
                20                  25                  30

Arg

<210> SEQ ID NO 27
<211> LENGTH: 29
<212> TYPE: PRT
<213> ORGANISM: Artificial Sequence
<220> FEATURE:
<223> OTHER INFORMATION: Synthetic peptide

<400> SEQUENCE: 27

Met Gln Ile Pro Gln Ala Pro Trp Pro Val Val Trp Ala Val Leu Gln
1               5                   10                  15

Leu Gly Trp Arg Arg Lys Lys Arg Arg Gln Arg Arg Arg

```
                20              25

<210> SEQ ID NO 28
<211> LENGTH: 31
<212> TYPE: PRT
<213> ORGANISM: Artificial Sequence
<220> FEATURE:
<223> OTHER INFORMATION: Synthetic peptide

<400> SEQUENCE: 28

Met Arg Ile Phe Ala Val Phe Ile Phe Met Thr Tyr Trp His Leu Leu
1               5                   10                  15

Asn Ala Lys Lys Arg Thr Leu Arg Lys Asn Asp Arg Lys Lys Arg
            20                  25                  30

<210> SEQ ID NO 29
<211> LENGTH: 33
<212> TYPE: PRT
<213> ORGANISM: Artificial Sequence
<220> FEATURE:
<223> OTHER INFORMATION: Synthetic peptide

<400> SEQUENCE: 29

Pro Trp Trp Trp Pro Pro Val Val Val Gln Gln Gln Met Leu Leu Ile
1               5                   10                  15

Gly Ala Ala Arg Lys Lys Arg Thr Leu Arg Lys Asn Asp Arg Lys Lys
            20                  25                  30

Arg

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide

<400> SEQUENCE: 30

Lys Lys Arg Thr Leu Arg Lys Asn Asp Arg Lys Lys Arg
1               5                   10
```

ANTITUMOR PEPTIDE HAVING PD-1 SIGNAL SEQUENCE AND UTILIZATION THEREOF

TECHNICAL FIELD

The present invention relates to an artificially synthesized antitumor peptide that can suppress proliferation of tumor cells and use thereof. More specifically, the present invention relates to use of an artificial peptide including an amino acid sequence comprising a signal peptide of PD-1 (hereinafter also referred to as "signal sequence") and a cell penetrating peptide sequence.

The present application is a national stage application filed under 35 U.S.C. § 371 of PCT/JP2018/012565 filed 27 Mar. 2018, which claims priority to Japanese Patent Application No. 2017-070758 filed on 31 Mar. 2017, which are entirely incorporated herein by reference.

BACKGROUND ART

Studies on cancer immunotherapy have progressed rapidly. Among others, "immune checkpoint-inhibitory therapy" is attracting attention. It can be said that the therapy is to utilize substances associated with so-called "immune checkpoint proteins" such as "cytotoxic T-lymphocyte associated antigen-4 (CTLA-4)" and "programmed cell death-1 (PD-1)" that are known proteins involved in functions to suppress excess immunoreaction in body as immune checkpoint inhibitors and blocking the "mechanism that avoids attack by immune system (also referred to as immunoescape mechanism)" in which cancer cells are involved, thereby encouraging or resuming attack by immune system to cancer cells.

It has been observed that administration of, for example, an antibody (anti-PD-1 antibody) against PD-1, which is a membrane protein belonging to the immunoglobulin superfamily, or an antibody (anti-PD-L1 antibody) against a ligand of PD-1 termed PD-L1 (programmed cell death-1 ligand-1: also referred to as B7-H1) that is commonly expressed on various cells including tumor cells as an immune checkpoint inhibitor to patients can block the immunoescape mechanism, thereby improving antitumor immunoreactivity of immune cells on some tumors (for examples, see Patent Literature 1).

CITATION LIST

Patent Literature

Patent Literature 1: WO 2004/004771

Non Patent Literature

Non Patent Literature 1: Microbiology and Immunology, vol. 54, 2010, pp. 291-298

SUMMARY OF INVENTION

However, anti-PD-1 antibodies and anti-PD-L1 antibodies may have substantially no or very low effects on an improvement of the antitumor immunoreactivity on some types of tumor, and thus it is necessary to develop immune checkpoint inhibitors further. Moreover, antitumor agents containing such antibodies as a medicinal component are very expensive, and a problem in cost of the cancer therapy can cause an unavoidable serious situation.

Thus, an object of the present invention is to provide a novel antitumor (which can be referred to as anticancer) synthetic peptide that has a different composition from antitumor agents containing expensive antibodies such as anti-PD-1 antibodies and anti-PD-L1 antibodies.

The inventors of the present invention focused on signal peptide regions of PD-1 expressed in various organisms, particularly, mammals Surprisingly, the inventors found that a synthetic peptide comprising an amino acid sequence that forms a signal peptide of PD-1 and an amino acid sequence that forms a conventionally-known cell penetrating peptide (CPP) in combination has excellent antitumor (anticancer) activity on various tumor cells, thereby completing the present invention.

Thus, the synthetic peptide disclosed herein is an antitumor peptide that may suppress proliferation of at least one type of tumor cells. The peptide is characterized in that the peptide contains both amino acid sequences indicated in following (1) and (2) below:

(1) an amino acid sequence composing a signal peptide of a membrane protein, programmed cell death-1 (PD-1), or a modified amino acid sequence formed by deletion, substitution or addition of 1, 2, or 3 amino acid residues in the amino acid sequence; and (2) an amino acid sequence functioning as a cell penetrating peptide (CPP).

In one preferable aspect, the total number of amino acid residues is 100 or less. In terms of production cost, easiness of synthesis, handling properties, more preferably, the total number of amino acid residues is 80 or fewer (such as 70 or fewer).

Alternatively, the synthetic peptide in which the sum of the numbers of amino acid residues in the amino acid sequences indicated in (1) and (2) accounts for 80% or more (more preferably 90% or more such as 100%) of the total number of amino acid residues in the whole antitumor peptide is a particularly suitable aspect of the antitumor peptide disclosed herein.

In another suitable aspect of the antitumor peptide disclosed herein, the amino acid sequence forming the signal peptide of PD-1 is an amino acid sequence represented by any one of SEQ ID NOs: 1 to 7.

In another suitable aspect of the antitumor peptide disclosed herein, the amino acid sequence functioning as the CPP is a polyarginine (typically formed of 5 or more and 9 or fewer arginine residues without particular limitation), or an amino acid sequence indicated in any of SEQ ID NOs: 8 to 25 or a modified amino acid sequence formed by deletion, substitution, or addition of 1, 2, or 3 amino acid residues in the amino acid sequence.

A suitable example is a synthetic peptide including both: (i) an amino acid sequence represented by any one of SEQ ID NOs: 1 to 7 or a modified amino acid sequence formed by deletion, substitution or addition of 1 or more (such as 2 or 3) amino acid residues in the amino acid sequence; and (ii) a polyarginine, or an amino acid sequence represented by any one of SEQ ID NOs: 8 to 25 or a modified amino acid sequence formed by deletion, substitution, or addition of 1 or more (such as 2 or 3) amino acid residues in the amino acid sequence.

The present invention also provides an antitumor composition that suppresses proliferation of at least one type of tumor cells, comprising any of the synthetic peptides (antitumor peptides) disclosed herein and at least one pharmaceutically acceptable carrier.

The composition contains the antitumor peptide disclosed herein, and thus can be used as an antitumor agent (encompassing an anticancer agent; the same applies hereinbelow) or can be used as a material for developing a novel antitumor agent.

The present invention also provides a method for suppressing proliferation of at least one type of tumor cells, including providing, at least once, any of the synthetic peptides (antitumor peptides) disclosed herein to tumor cells of interest (for example, in vitro or in vivo).

According to the method as above, the antitumor peptide disclosed herein is provided to tumor cells, and thus proliferation of the tumor cells (as a result, enlargement of tumor and cancer tissues) can be blocked or suppressed.

DESCRIPTION OF EMBODIMENTS

Suitable embodiments of the present invention are hereinafter described. The matters that are essential for implementation of the present invention (such as general matters associated with chemical synthesis methods of peptides, cell culture methods and preparation of pharmaceutical compositions containing peptides) other than the matters particularly referred to in the present specification (such as the primary structure and length of the synthetic peptide disclosed herein) can be understood as design matters for a person skilled in the art based on the background art in the fields of cell engineering, physiology, medical science, pharmaceutical science, organic chemistry, biochemistry, genetic engineering, protein engineering, molecular biology, genetics and the like. The present invention may be implemented on the basis of the contents disclosed herein and common technical knowledge in the art. In the descriptions hereinbelow, amino acids are represented by one-letter representations (by three-letter representations in the Sequence Listing).

The entire contents of all documents cited herein are incorporated herein by reference.

The term "tumor" as used herein is interpreted in a broad sense and refers to general tumors (typically malignant tumors) including carcinoma and sarcoma or lesions in blood and hematopoietic tissues (such as leukemia and lymphoma). The term "tumor cells" is synonymous with "cancer cells" and refers to cells that form such a tumor and typically are resulted in abnormal proliferation (so-called malignantly transformed cells) irrelevantly to surrounding normal tissues. Therefore, unless otherwise defined, any cells classified to tumor cells (cancer cells) rather than normal cells are referred to as tumor cells irrespective of the source or properties of the cells. Cells that form epithelial tumor (such as squamous cell carcinoma and adenocarcinoma), non-epithelial tumor (such as various types of sarcoma and osteosarcoma), various types of carcinoma (such as neuroblastoma and retinoblastoma), lymphoma, melanoma and the like are typical examples that are encompassed by tumor cells as used herein.

The term "synthetic peptide" as used herein refers to a peptide fragment of which peptide chain does not stably and independently occur in nature and that is produced by artificial chemical synthesis or biosynthesis (namely production based on genetic engineering) and may stably exist in certain compositions. The term "peptide" as used herein refers to an amino acid polymer having more than one peptide bond and is not limited by the number of amino acid residues included in the peptide chain. However, the term typically refers to those having a relatively low molecular weight such that the number of total amino acid residues is generally 100 or fewer (preferably 80 or fewer, more preferably 70 or fewer and particularly preferably 50 or fewer).

The term "amino acid residue(s)" as used herein encompasses, unless otherwise stated, an N-terminal amino acid and a C-terminal amino acid of a peptide chain.

The N-terminus is always on the left and the C-terminus is on the right of amino acid sequences described herein.

A "modified amino acid sequence" for a certain amino acid sequence as used herein refers to an amino acid sequence that is formed by substitution, deletion or addition (insertion) of one to several (typically 9 or fewer, preferably 5 or fewer) amino acid residues such as 1, 2 or 3 amino acid residues without deteriorating the function (such as antitumor activity and cell penetrating ability) of the certain amino acid sequence. Typical examples that are encompassed by the modified amino acid sequence as used herein include sequences generated by so-called conservative amino acid substitution in which 1, 2 or 3 amino acid residues are conservatively substituted (for example, sequences obtained by substituting a basic amino acid residue with another basic amino acid residue: such as mutual substitution between a lysine residue and an arginine residue) and sequences which are obtained adding (inserting) 1, 2 or 3 amino acid residues to or deleting 1, 2 or 3 amino acid residues from a certain amino acid sequence. Therefore, the antitumor peptide disclosed in Examples herein encompass, in addition to synthetic peptides formed from the amino acid sequences identical to the amino acid sequences of the respective SEQ ID NOs, synthetic peptides consisting of modified amino acid sequences formed by substitution (such as conservative amino acid substitution), deletion, or addition of 1, 2 or 3 amino acid residues in the amino acid sequences of the respective SEQ ID NOs and which exhibit similar antitumor activity.

The artificially synthesized antitumor peptide disclosed herein is a short-chain peptide that does not occur naturally and is characterized in that the peptide contains both amino acid sequences described above, namely:
(1) an amino acid sequence comprising a signal peptide of PD-1 or a modified amino acid sequence formed by deletion, substitution or addition of 1, 2, or 3 amino acid residues in the amino acid sequence while retaining its antitumor activity; and
(2) an amino acid sequence functioning as a CPP.

PD-1 is a membrane protein typically formed of approximately 270 to 290 amino acid residues, belonging to the immunoglobulin superfamily, and is an immune checkpoint protein, in other words, a protein involved in negative regulation of immune reactions in vivo.

However, it has not been found that a signal peptide region of PD-1 has an antitumor activity, and it was not envisaged at the time of filing the present application that an artificially synthesized antitumor peptide could be obtained by synthesizing an amino acid sequence of the signal peptide region and adding a CPP to the sequence.

As disclosed in, for example, Non Patent Literature 1, genes (including cDNAs) encoding PD-1 have been found in mammals such as humans, chimpanzees, cattle, mice, rats, cats and ferrets and birds such as chickens. Genetic information and amino acid sequence information of PD-1 can be obtained by accessing to knowledge bases (data bases) of various public international organizations. Information on full-length amino acid sequence and amino acid sequence of signal peptide regions of PD-1 derived from various organisms is available in, for example, the Universal Protein Resource (UniProt).

Without intending any particular limitation, suitable examples of the amino acid sequence that forms a signal peptide of PD-1 are indicated in SEQ ID NOs: 1 to 7. Specifically, the sequences are as follows:

SEQ ID NO: 1 is a signal sequence consisting of total 20 amino acid residues in PD-1 derived from humans;

SEQ ID NO: 2 is a signal sequence consisting of total 20 amino acid residues in PD-1 derived from mice;

SEQ ID NO: 3 is a signal sequence consisting of total 29 amino acid residues in PD-1 derived from cattle;

SEQ ID NO: 4 is a signal sequence consisting of total 29 amino acid residues in PD-1 derived from buffaloes;

SEQ ID NO: 5 is a signal sequence consisting of total 24 amino acid residues in PD-1 derived from cats;

SEQ ID NO: 6 is a signal sequence consisting of total 20 amino acid residues in PD-1 derived from monkeys (such as chimpanzees); and SEQ ID NO: 7 is a signal sequence consisting of total 20 amino acid residues in PD-1 derived from rats.

The amino acid sequence functioning as a CPP used for forming the antitumor peptide disclosed herein may be any conventionally-known CPP. A so-called polyarginine (Rn) consisting of, for example, 3 or more, preferably 5 or more and 11 or fewer, preferably 9 or fewer arginine residues is a CPP that is suitably used herein. Alternatively, any known CPP may be used.

Without intending any particular limitation, suitable examples of the CPP are indicated in SEQ ID NOs: 8 to 25. Specifically, the sequences are as follows:

the amino acid sequence in SEQ ID NO: 8 corresponds to a NoLS (Nucleolar localization signal) consisting of a total of 14 amino acid residues derived from FGF2 (basic fibroblast growth factor);

the amino acid sequence of SEQ ID NO: 9 corresponds to a NoLS consisting of total 19 amino acid residues derived from a nucleolar protein (ApLLP);

the amino acid sequence of SEQ ID NO: 10 corresponds to a NoLS consisting of total 16 amino acid residues derived from a protein (γ(1)34.5) of HSV-1 (herpes simplex virus type 1);

the amino acid sequence of SEQ ID NO: 11 corresponds to a NoLS consisting of total 19 amino acid residues derived from a p40 protein of HIC (human I-mfa domain-containing protein);

the amino acid sequence of SEQ ID NO: 12 corresponds to a NoLS consisting of total 16 amino acid residues derived from MEQ protein of MDV (Marek disease virus);

the amino acid sequence of SEQ ID NO: 13 corresponds to a NoLS consisting of total 17 amino acid residues derived from an inhibitory protein of apoptosis, Survivin-deltaEx3;

the amino acid sequence of SEQ ID NO: 14 corresponds to a NoLS consisting of total 7 amino acid residues derived from a vascular growth factor, Angiogenin;

the amino acid sequence of SEQ ID NO: 15 corresponds to a NoLS consisting of total 8 amino acid residues derived from a nuclear phosphoprotein, MDM2, which forms a complex with p53 tumor suppressor protein;

the amino acid sequence of SEQ ID NO: 16 corresponds to a NoLS consisting of total 9 amino acid residues derived from a betanoda virus protein, GGNNVα;

the amino acid sequence of SEQ ID NO: 17 corresponds to a NoLS consisting of total 7 amino acid residues derived from NF-κB-inducing kinase (NIK);

the amino acid sequence of SEQ ID NO: 18 corresponds to a NoLS consisting of total 15 amino acid residues derived from Nuclear VCP-like protein;

the amino acid sequence of SEQ ID NO: 19 corresponds to a NoLS consisting of total 18 amino acid residues derived from a nucleolar protein, p120;

the amino acid sequence of SEQ ID NO: 20 corresponds to a NoLS consisting of total 14 amino acid residues derived from ORF57 protein of HVS (herpesvirus saimiri);

the amino acid sequence of SEQ ID NO: 21 corresponds to a NoLS consisting of total 13 amino acid residues from the 491st amino acid residue to the 503rd amino acid residue of a protein kinase involved in intracellular signaling, LIM kinase 2, present in human endothelial cells;

the amino acid sequence of SEQ ID NO: 22 corresponds to a NoLS consisting of total 8 amino acid residues included in a N protein (nucleocapsid protein) of IBV (avian infectious bronchitis virus);

the amino acid sequence of SEQ ID NO: 23 corresponds a cell penetrating motif consisting of total 9 amino acid sequences derived from a protein transduction domain in TAT of HIV (Human Immunodeficiency Virus);

the amino acid sequence of SEQ ID NO: 24 corresponds a cell penetrating motif consisting of total 11 amino acid sequences of a protein transduction domain (PTD4) obtained by modifying the above TAT; and the amino acid sequence of SEQ ID NO: 25 corresponds a cell penetrating motif consisting of total 18 amino acid sequences derived from an ANT from Antennapedia which is a mutant of *Drosophila*.

Among others, amino acid sequences (or modified amino acid sequences thereof) associated with NoLS and TAT are particularly preferred. For example, CPP sequences associated with NoLS such as those indicated in SEQ ID NO: 21 and SEQ ID NO: 22, or CPP sequences associated with TAT and ANT of SEQ ID NOs: 23 to 25 may be suitably used for forming the antitumor peptide disclosed herein.

It is enough for the peptide chain (amino acid sequence) of the antitumor peptide disclosed herein to contain, as described above, (1) an amino acid sequence forming a signal peptide of PD-1 or a modified amino acid sequence thereof (hereinafter also referred to as "PD-1 SP-related sequence"); and (2) an amino acid sequence functioning as a CPP (hereinafter also referred to as "CPP-related sequence"), and either the PD-1 SP-related sequence or the CPP-related sequence may be provided at the N-terminal side (C-terminal side) relative to the other one.

It is preferable that the PD-1 SP-related sequence and CPP-related sequence are provided so that the sequences are substantially adjacent. Specifically, there is no amino acid residue that does not belong to the sequences of the PD-1 SP-related sequence and the CPP-related sequence between the sequences. Alternatively, even if there are amino acid residues therebetween, the number of the amino acid residues is preferably 10 or fewer (more preferably 5 or fewer such as 1 or 2 amino acid residues).

Unless an antitumor activity that may suppress proliferation of at least one type of tumor cells is eliminated, the antitumor peptide may contain a sequence (amino acid residues) that does not belong to the amino acid sequences forming the PD-1 SP-related sequence and the CPP-related sequence.

The antitumor peptide disclosed herein appropriately contains total 100 or fewer, preferably 80 or fewer and preferably 70 or fewer amino acid residues forming the peptide chain (such as a peptide chain containing around 30 to around 50 residues). Such a peptide with a short chain length can be easily synthesized by chemical synthesis and thus the antitumor peptide can be easily provided. Without intending any particular limitation, because of a less chance of serving as an immunogen (antigen), the peptide is preferably linear or helical. The peptide in such a form hardly forms an epitope.

The proportion of the sum of the numbers of amino acid residues in the PD-1 SP-related sequence and the CPP-related sequence relative to the total number of amino acid residues in the synthesized whole peptide is not particularly limited unless the antitumor activity is eliminated. However, the proportion is generally preferably 80% or more and preferably 90% or more. Although it is preferable that all amino acid residues are L-amino acids, some or all amino acid residues may be replaced by D-amino acids unless the antitumor activity is eliminated.

Preferably, the antitumor peptide disclosed herein preferably contains at least one amidated amino acid residue. By amidation of a carboxyl group of an amino acid residue (typically a C-terminal amino acid residue of the peptide chain), the synthetic peptide may have improved structural stability (such as protease resistance).

The antitumor peptide disclosed herein may be easily produced according to general chemical synthesis methods. For examples, any of conventionally-known solid phase synthesis methods or liquid-phase synthesis methods may be used. The solid-phase synthesis method in which Boc (t-butyloxycarbonyl) or Fmoc (9-fluorenylmethoxycarbonyl) is used as a protective group of an amino group is suitable.

The antitumor peptide disclosed herein may be synthesized as a peptide chain having a desired amino acid sequence and a modification (such as C-terminal amidation) moiety by a solid phase synthesis method using a commercially available peptide synthesizer.

Alternatively, the antitumor peptide may be biosynthesized by genetic engineering approaches. Namely, a polynucleotide (typically DNA) of a nucleotide sequence (including the ATG start codon) encoding an amino acid sequence of a desired antitumor peptide is synthesized. A recombinant vector is constructed according to a host cell, the vector including a gene construct for expression containing the synthesized polynucleotide (DNA) and various regulatory elements (including a promoter, a ribosome binding site, a terminator, an enhancer and various cis-acting elements controlling the expression level) for expression of the amino acid sequence in the host cell.

The recombinant vector is introduced into a certain host cell (such as yeast, insect cell or plant cell) according to a general method and the host cell or a tissue or individual containing the cell is cultured under certain conditions. As a result of this, the peptide of interest may be expressed and produced in the cell. The peptide may be then isolated from the host cell (from a culture medium when the peptide is secreted), and optionally subjected to refolding, purification or the like to give the antitumor peptide of interest.

The method for constructing the recombinant vector, the method for introducing the constructed recombinant vector into the host cell may be the methods that have been conventionally employed in the art, and the methods per se are not characteristic of the present invention. Therefore, detailed descriptions thereon are omitted.

Alternatively, the polypeptide of interest may be synthesized in vitro by constructing a template DNA (i.e. a synthetic gene fragment containing a nucleotide sequence encoding an amino acid sequence of the antitumor peptide) for a cell-free protein synthesis system, using various compounds (such as ATP, RNA polymerase, amino acids) necessary for peptide synthesis and employing a so-called cell-free protein synthesis system. For the cell-free protein synthesis system, a research paper by Shimizu et al. (Shimizu et al., Nature Biotechnology, 19, 751-755 (2001)) and a research paper by Madin et al. (Madin et al., Proc. Natl. Acad. Sci. USA, 97(2), 559-564 (2000)), for example, may be referred to. On the basis of the techniques disclosed in the research papers, many companies are already conducting contract manufacturing of polypeptides at the time of filing of the present application, and cell-free protein synthesis kits (such as those available from CellFree Sciences Co., Ltd., Japan) are commercially available.

A single-stranded or double-stranded polynucleotide containing a nucleotide sequence encoding the antitumor peptide disclosed herein and/or a complementary nucleotide sequence thereto may be easily produced (synthesized) according to conventionally-known methods. Namely, by selecting codons for amino acid residues included in a designed amino acid sequence, a nucleotide sequence for an amino acid sequence of the antitumor peptide is easily defined and provided. Once the nucleotide sequence is defined, a polynucleotide (single strand) corresponding to the desired nucleotide sequence may be easily obtained by using a DNA synthesizer or the like. Further, by using the obtained single-stranded DNA as a template, a double-stranded DNA of interest may be obtained by employing any enzymatic synthesis method (typically PCR). The polynucleotide may be in the form of DNA or RNA (such as mRNA). DNA provided may be double-stranded or single-stranded. When the DNA provided is single-stranded, the DNA may be a coding strand (sense strand) or a non-coding strand (antisense strand) complementary thereto.

The polynucleotide thus obtained may be used as a material for constructing a recombinant gene (expression cassette) for production of the antitumor peptide in, as described above, any host cell or cell-free protein synthesis system.

The antitumor peptide disclosed herein may be suitably used as an active ingredient of a composition (namely, a pharmaceutical antitumor composition such as an antitumor agent) for suppression (or inhibition) of proliferation of tumor cells. The antitumor peptide may be in the form of a salt unless the antitumor activity is eliminated. For example, an acid addition salt of the synthetic peptide may be used that may be obtained by addition reaction of an inorganic acid or organic acid that is commonly used according to a conventional method. Therefore, the "peptide(s)" recited in the present description and claims encompasses those in the form of salts.

The antitumor composition disclosed herein may contain any pharmaceutically (medically) acceptable carrier according to the form of usage unless the antitumor activity of the antitumor peptide which is the active ingredient is eliminated. For example, a carrier that is generally used in peptide medicines as a diluent, a vehicle or the like may be used.

Although it may vary, as appropriate, according to the application or form of the antitumor composition disclosed herein, typical carriers include water, phosphate buffered saline and various organic solvents. The carrier may be an alcohol (such as ethanol) aqueous solution with an appropriate concentration, glycerol or non-drying oil such as olive oil. The carrier may alternatively be a liposome. Examples of auxiliary components that may be added to the antitumor composition include various fillers, bulking agents, binding agents, wetting agents, surfactants, colorants and perfumes.

Typical forms of the antitumor composition (antitumor agent) include solutions, suspensions, emulsions, aerosol, foam, granules, powders, tablets, capsules, ointments, aqueous gels and the like. The antitumor composition (antitumor agent) may be freeze dried or granulated in order to be dissolved in saline or an appropriate buffer (such as PBS) immediately before use to prepare a solution to be used for injections and the like.

The process per se by which a composition (drug) in any form is prepared from materials including the antitumor peptide (main component) and various carriers (auxiliary components) may follow conventionally-known methods, and the production method per se is not characteristic of the present invention. Therefore, detailed descriptions thereof are omitted. Examples of the source of detailed information of formulations include Comprehensive Medicinal Chemistry, Corwin Hansch editor-in-chief, published by Pergamon Press (1990). The entire content thereof is incorporated herein by reference.

The cells to which the antitumor composition (antitumor peptide) disclosed herein is applied are not particularly limited as long as the cells are tumor cells (cancer cells), and the antitumor composition (antitumor peptide) may be applied to various types of tumor cells generated in humans or non-human mammals. Examples of the cells include various types of squamous cell carcinoma and adenocarcinoma. Examples of the cells include cancer cells of breast cancer, pancreatic cancer, prostate cancer, lung cancer (non small cell lung cancer and small cell lung cancer) and the like and cells included in skin cancer such as melanoma and basal cell cancer, neuroblastoma, retinoblastoma, pheochromocytoma and other carcinoma.

The antitumor composition disclosed herein may be used by a method and at a dose according to the form and purpose thereof, as conventional peptide preparations. For example, the antitumor composition may be administered as a solution at a desired dose to a diseased site (typically malignant tumor tissue) of a patient (namely a living body) by an intravenous, intramuscular, subcutaneous, intradermal or intraperitoneal injection. Alternatively, the antitumor composition in the form of solid such as tablets or gel or aqueous jelly such as ointment may be administered directly to a certain tissue (namely a diseased site of tissue or organ containing tumor cells). Alternatively, the antitumor composition in the form of solid such as tablets may be orally administered. In case of oral administration, it is preferable to encapsulate or use a protective (coating) material in order to block decomposition by digestive enzymes in the digestive tract.

Alternatively, to tumor cells (including cell mass or tissue or organ excised from a living body) cultured in vitro, an appropriate amount (namely an appropriate amount of the antitumor peptide) of the antitumor composition disclosed herein may be provided to a medium of cultured cells (such as tissue) to be treated at least once. The amount per dose and frequency of provision may vary according to the conditions such as the type of the cultured tumor cells, cell density (cell density at the beginning of culture), the number of subcultures, culture conditions and the type of the medium, and thus are not particularly limited. It is preferable that the antitumor composition is added once to several times so that the antitumor peptide concentration in the medium is generally in the range of 5 μM or more and 100 μM or less and preferably in the range of 10 μM or more and 50 μM or less (such as 12.5 μM or more and 25 μM or less).

Some Examples pertaining to the present invention are hereinafter described. However, it is not intended to limit the present invention to the Examples.

TABLE 1

| Sample No. | Amino acid sequence | Number of total amino acid residues |
|---|---|---|
| 1 | MQIPQAPWPVVWAVLQLGWRKKRTLRK NDRKKR-$_{CONH2}$ (SEQ ID NO: 26) | 33 |
| 2 | MQIPQAPWPVVWAVLQLGWRRKKRRQR RR-$_{CONH2}$ (SEQ ID NO: 27) | 29 |
| 3 | MRIFAVFIFMTYWHLLNAKKRTLRKND RKKR-$_{CONH2}$ (SEQ ID NO: 28) | 31 |
| 4 | PWWWPPVVVQQQMLLIGAARKKRTLRK NDRKKR-$_{CONH2}$ (SEQ ID NO: 29) | 33 |
| 5 | KKRTLRKNDRKKR-$_{CONH2}$ (SEQ ID NO: 30) | 13 |

Test Example 1: Synthesis of Peptides

Five peptides indicated in Table 1 were produced on a commercially available peptide synthesizer. Specifically, the peptides were as follows:

sample 1 was designed as one of Examples, and is a synthetic peptide containing the amino acid sequence of SEQ ID NO: 21 (NoLS of LIM kinase 2) as a CPP-related sequence on the C-terminal side of a signal sequence of human PD-1 (SEQ ID NO: 1);

sample 2 was designed as one of Examples, and is a synthetic peptide containing the amino acid sequence of SEQ ID NO: 23 (TAT of HIV) as a CPP-related sequence on the C-terminal side of a signal sequence of human PD-1 (SEQ ID NO: 1);

sample 3 was designed as a comparison, and is a synthetic peptide containing the amino acid sequence of SEQ ID NO: 21 (NoLS of LIM kinase 2) as a CPP-related sequence on the C-terminal side of a signal sequence of human PD-L1;

sample 4 was designed as a comparison, and is a synthetic peptide containing the amino acid sequence of SEQ ID NO: 21 (NoLS of LIM kinase 2) as a CPP-related sequence on the C-terminal side of the sequence of randomly rearranged amino acids in the signal sequence of human PD-1; and sample 5 was designed as a comparison, and is a synthetic peptide consisting of the amino acid sequence of SEQ ID NO: 21 (NoLS of LIM kinase 2) which is a CPP-related sequence.

The peptides of samples 1 to 5 above were all synthesized on a commercially available peptide synthesizer by carrying out exactly the same solid phase synthesis method (Fmoc method) as described in the instruction manual of the synthesizer. The way of usage per se of the peptide synthesizer is not characteristic of the present invention, and thus detailed descriptions thereon are omitted. In all synthetic peptides, carboxyl groups (—COOH) of C-terminal amino acids are amidated (—CONH$_2$).

The synthesized sample peptides were dissolved in DMSO (dimethyl sulfoxide) to prepare stock solutions (concentration: 2.5 mM) of sample peptides.

Test Example 2: Evaluation Test on Antitumor Activities of Synthetic Peptides

Some of the sample peptides synthesized in Test Example 1 were evaluated for antitumor activity on several types of cultured tumor cells.

Specifically, test tumor cells used were currently commercially available human non small cell lung cancer cell line (NCI-H2444), human non small cell lung cancer cell line (HCC827), human alveolar basal epithelial adenocarcinoma cell line (A549), human small cell lung cancer cell line (NCI-H446), human melanoma cell line (A2058) and human breast adenocarcinoma cell line (MDA-MB-231). As a comparison, a commercially available cultured normal human mammary epithelial cell line (MCF-12F) was used.

The following media were used for culture of the cell lines:

(1) human non small cell lung cancer cell line (NCI-H2444), human non small cell lung cancer cell line (HCC827), human alveolar basal epithelial adenocarcinoma cell line (A549) and human small cell lung cancer cell line (NCI-H446):

RPMI-1640 medium (product from Wako Pure Chemical Industries, Ltd.) containing 2 mM L-glutamine, 1 mM sodium pyruvate, 10 mM HEPES, 4500 mg/mL glucose, 50 units/mL penicillin, 50 μg/mL streptomycin and 10% fetal bovine serum (FBS);

(2) human melanoma cell line (A2058) and human breast adenocarcinoma cell line (MDA-MB-231):

DMEM medium (product from Wako Pure Chemical Industries, Ltd.) containing 2 mM L-glutamine, 0.1 mM non-essential amino acids, 50 units/mL penicillin, 50 μg/mL streptomycin and 10% FBS; and (3) cultured normal human mammary epithelial cell line (MCF-12F):

DMEM/F12 medium (product from Wako Pure Chemical Industries, Ltd.) containing 20 ng/mL recombinant EGF, 10 μg/mL insulin, 0.5 μg/mL hydrocortisone and 10% FBS.

The details of the test are indicated below.

The above six cell lines were cultured in each of the media indicated above and the number of cells was adjusted to be approximately $5\times10^3$ per well in a 96-well plate. The amount of the medium was 100 μL per well.

The 96-well plate was placed in a $CO_2$ incubator and pre-incubated under conditions of 37° C. and 5% $CO_2$ for approximately one day (21 hours to 24 hours).

Thereafter, peptide-containing test media were respectively prepared for each concentration so that the concentration of any of the sample peptides to be evaluated was either 12.5 μM or 25 μM, and were supplied to wells (namely, wells after pre-incubation above) in which cells to be evaluated were cultured at 90 μL per well. The 96-well plate was placed back in the $CO_2$ incubator and incubated under conditions of 37° C. and 5% $CO_2$ for 48 hours.

The number (n) of test wells per each peptide concentration in the test section to which peptides were added was 3. Therefore, the values indicated in the result section in the table hereinbelow are averages of results obtained from 3 test wells. The cell viability (%) was determined as indicated hereinbelow.

After a 48-hour incubation, the medium in the wells was replaced by 100 μL fresh medium without peptide, and 10 μL of a reagent for cell proliferation measurement "Cell Counting Kit-8" (product from Dojindo Laboratories) containing "water-soluble tetrazolium salt (WST-8)" as a chromogenic reagent was added to each well. The 96-well plate was then placed back in the $CO_2$ incubator and incubated under conditions of 37° C. and 5% $CO_2$ for 1.5 hours to 2 hours.

After completion of the incubation, the cell culture medium to which the reagent was added was recovered and the cell viability (%) was evaluated by a colorimetric method in which the absorbance at a wavelength of 450 nm (the value corrected with the absorbance at a wavelength 650 nm: A450-A650) due to reduction of the tetrazolium salt was measured. Specifically, the cell viability (%) of each test cell line was calculated from the measured absorbance as a relative value to the measured value (measured absorbance) in the comparative test section in which the incubation over 48 hours as above was carried out only with a medium without peptide, that was regarded as 100% of the cell viability. The results are indicated in Table 2.

TABLE 2

| | | Cell viability (%) | |
|---|---|---|---|
| | | | Test peptide concentration |
| Test cell line | Test sample No. | 12.5 μM | 25.0 μM |
| Non small cell lung cancer (NCI-H2444) | No. 1 | 59.6 | 6.8 |
| | No. 2 | 50.4 | 3.6 |
| | No. 3 | 106.3 | 87.7 |
| Non small cell lung cancer (HCC827) | No. 1 | 49.8 | 11.8 |
| | No. 2 | 62.9 | 4.9 |
| | No. 3 | 105.4 | 120.6 |
| | No. 4 | 110.9 | 102.6 |
| | No. 5 | 106.7 | 106.5 |
| Alveolar basal epithelial adenocarcinoma (A549) | No. 2 | 52.4 | 9.1 |
| Small cell lung cancer (NCI-H446) | No. 1 | 2.5 | 0.5 |
| | No. 3 | 67.9 | 56.7 |
| Melanoma (A2058) | No. 1 | 50.4 | 6.7 |
| | No. 3 | 100.9 | 87.5 |
| Breast adenocarcinoma (MDA-MB-231) | No. 1 | 63.1 | 9.9 |
| | No. 3 | 89.3 | 83.7 |
| Normal mammary epithelial cell (MCF-12F) | No. 1 | 97.4 | 62.3 |
| | No. 3 | 87.3 | 81.7 |

As apparent from the results shown in Table 2, it was found that the both synthetic peptides of sample 1 and sample 2 each containing both the PD-1 SP-related sequence and the CPP-related sequence had excellent antitumor activity (inhibitory activity of proliferation of tumor cells) on tumor cells tested in the present Test Example compared to comparative samples 3 to 5. Particularly, excellent antitumor activity was found on small cell lung cancer. This indicates that the antitumor peptide disclosed herein may suppress proliferation of human tumor cells.

Although detailed data are not shown, synthetic peptides containing, as the PD-1 SP-related sequence, PD-1 SP-related sequences derived from a few types of non-human mammals (such as cattle and mice) together with a CPP-related sequence were found to have similar antitumor activity in a primary in vitro culture test, and thus usefulness of the synthetic peptide containing both the PD-1 SP-related sequence and the CPP-related sequence as an antitumor peptide has been demonstrated.

INDUSTRIAL APPLICABILITY

As described above, the antitumor peptide disclosed herein can suppress (or inhibit) proliferation of tumor cells. Because of this, by using the antitumor peptide provided by the present invention, an antitumor composition (antitumor agent) that suppresses proliferation of at least one type of tumor cells may be provided.

SEQUENCE LISTING FREE TEXT

SEQ ID NOs: 1 to 30 Synthetic peptides

The invention claimed is:

1. A synthetic peptide that suppresses proliferation of at least one type of tumor cell, the synthetic peptide comprising an amino acid sequence represented by SEQ ID NO: 26 or SEQ ID NO 27,
wherein the total number of amino acid residues is 100 or less.

2. An antitumor composition suppressing proliferation of at least one type of tumor cell, comprising:
a synthetic peptide; and
at least on pharmaceutically acceptable carrier,
wherein the synthetic peptide comprises an amino acid sequence represented by SEQ ID NO: 26 or SEQ ID NO: 27,
and the total number of amino acid residues is 100 or less.

3. A method for suppressing proliferation of at least one type of tumor cell, comprising: providing, at least once, a synthetic peptide to tumor cells of interest in vitro or in vivo, wherein the synthetic peptide comprises an amino acid represented by SEQ ID NO: 26 or SEQ ID NO: 27, and the total number of amino acid residues is 100 or less.

* * * * *